United States Patent [19]

Kulisz et al.

[11] Patent Number: 5,701,916
[45] Date of Patent: Dec. 30, 1997

[54] INTRAURETHRAL BLADDER CONTROL DEVICE WITH RETAINER APPARATUS

[75] Inventors: Andre A. Kulisz; Valery Migachyov, both of San Antonio, Tex.

[73] Assignee: HK Medical Technologies Incorporated, San Antonio, Tex.

[21] Appl. No.: 515,920

[22] Filed: Aug. 16, 1995

[51] Int. Cl.⁶ .................................................. A61F 5/48
[52] U.S. Cl. ........................... 128/885; 128/DIG. 25; 600/29
[58] Field of Search ................. 128/885, DIG. 25; 600/29-31; 604/329, 330

[56] References Cited

U.S. PATENT DOCUMENTS

| | | | |
|---|---|---|---|
| 3,628,530 | 12/1971 | Schwartz | 128/839 |
| 3,812,841 | 5/1974 | Isaacson | 128/DIG. 25 |
| 4,246,896 | 1/1981 | Horne | 128/833 |
| 5,041,092 | 8/1991 | Barwick | 128/DIG. 25 |
| 5,140,999 | 8/1992 | Ardito | 128/885 |

FOREIGN PATENT DOCUMENTS

WO 96/18431  6/1996  WIPO.

*Primary Examiner*—Michael A. Brown
*Attorney, Agent, or Firm*—Nawrocki, Rooney & Sivertson

[57] ABSTRACT

An improved intraurethral bladder control apparatus including housing means having a fluid flow path therethrough, valve means mounted within the fluid valve path and normally bias closed, the valvings responsive to pressure from fluid within the bladder of the patient for opening to allow fluid flow from the bladder through the apparatus of this invention and out of the urethra. A pair of retaining devices are connected to each of the distal and proximal ends of the intraurethral bladder control apparatus. The retainer at the distal end of the apparatus preferably comprises a leaf spring having a plurality of leaves, in the preferred embodiment described herein the plurality comprising four leaves, with a safety device connected to the tip of each leaf to inhibit piercing of the bladder wall when the leaves of the distal end retainer automatically open within the bladder of the patient after placement of the intraurethral bladder control apparatus. The proximal or lower retainer connects to the proximal end of the bladder control apparatus after it is placed in the urethra of the patient, and a portion of the lower retainer abuts the labia.

5 Claims, 5 Drawing Sheets

INTRAURETHRAL BLADDER CONTROL DEVICE WITH RETAINER APPARATUS

BACKGROUND OF THE INVENTION

1. Field of the Invention

The present invention generally relates to the field of medical devices and more particularly to intraurethral bladder control devices, and still more particularly to intraurethral bladder control devices with retaining means.

2. Description of the Prior Art

The use of bladder control devices, often referred to as artificial sphincters, is wide spread in the field of the present invention. The use of such intraurethral valving apparatus and its general knowledge in the field of art can be evidenced by, for example, U.S. Pat. Nos. 4,553,533; 4,679,546; 4,969,474; and 5,123,428.

A continuing problem found in the prior art devices is the safe and secure retention of the bladder control or valving device in the urethra. It is desirable to have the placement of the bladder control apparatus in the urethra be a nonsurgical function, and it is important not only that the device be securely retained once placed in the urethra, but also that a nonsurgical, safe and reasonably simple means of removing the device be present. Various prior art devices have not met all of these criteria.

SUMMARY OF THE INVENTION

The apparatus of this invention overcomes problems existent in the prior art by providing an improved intraurethral bladder control device with retainer apparatus. Broadly speaking, the apparatus of this invention comprises housing having an internal fluid flow path and valving means mounted in the fluid flow path and responsive to pressure from a patient's bladder to open and close the path to the flow of fluid from the bladder. A first retainer is mounted to the distal end of the housing and operates within the bladder to hold the bladder control apparatus within the urethra. In the preferred embodiment described herein, this first retainer comprises a leaf spring having a plurality of leaves which are compressed during placement of the bladder control device into the urethra, which leaves spring open when the distal end of the bladder control device reaches the opening into the bladder from the urethra. As used throughout this disclosure, the term "distal end" shall mean the end of a device or internal lumen which is intended to be closest to the bladder, and the term "proximal end" shall mean the end of the device or lumen which is closest to the urethral labia.

The apparatus of this invention also includes a second retainer which is connected to the proximal end of the bladder control device after its placement in the urethra, and which second retainer extends proximately out of the urethra where a portion thereof wider than the urethra abuts the urethral labia.

From the above brief description it can be seen that what is provided is a bladder control apparatus which is retained in a patient's urethra by a first retaining means operable within the bladder and by a second retaining means abutting the labia of the urethra. Thus a secure and safe system is provided for an intraurethral bladder control device.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which drawings like reference numerals designate like parts throughout the figures thereof, and wherein.

DETAILED DESCRIPTION OF THE PREFERRED EMBODIMENTS

Figure 1:
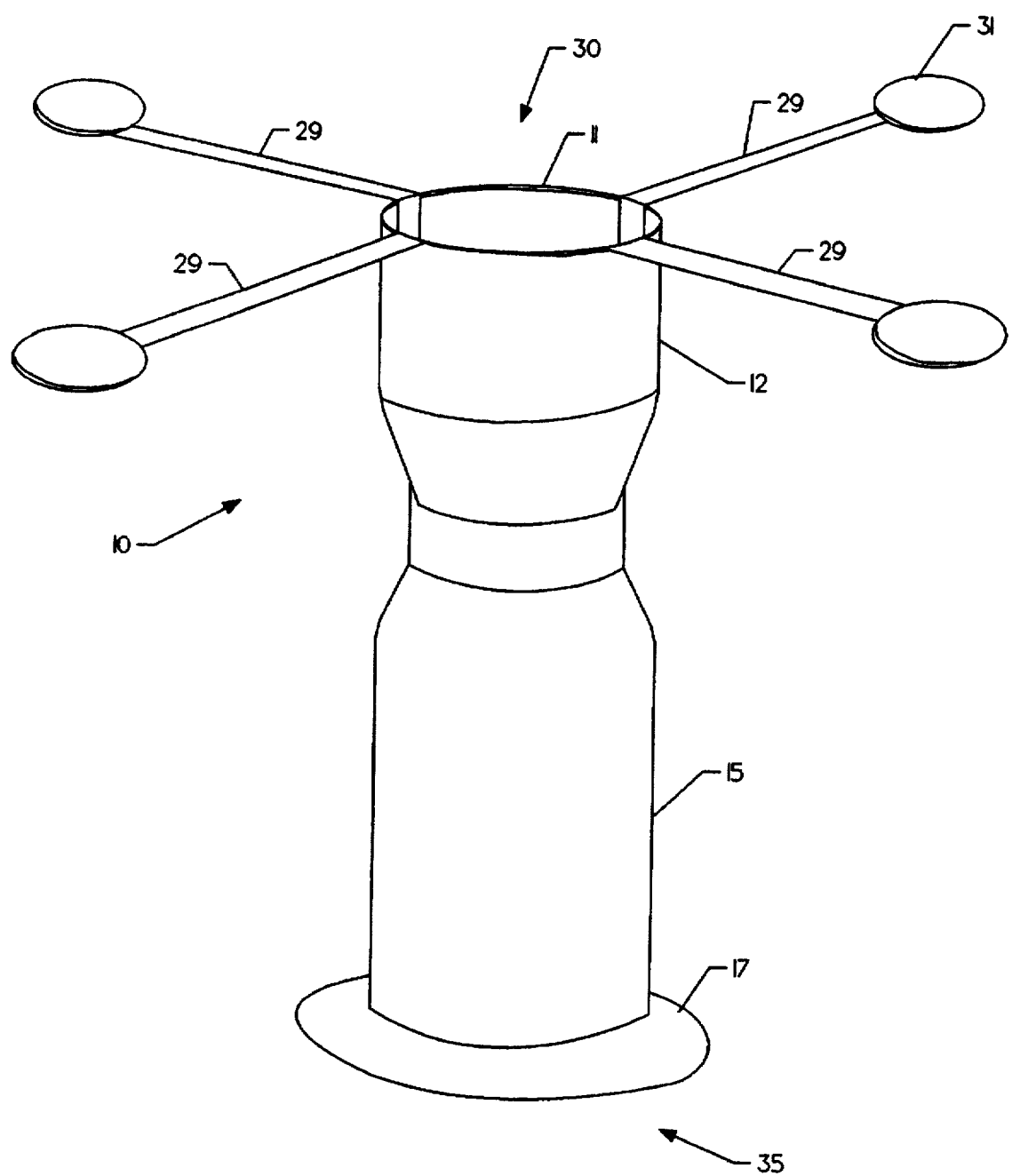
FIG. 1 is a perspective view representative of the apparatus of this invention.

FIG. 1 discloses a perspective view of the bladder control device 10 of this invention. It can be seen that the device 10 includes an upper or retainer housing 12 and a lower or full control housing 15. The distal end of housing 15 is connected to the proximal end of housing 12 such that an internal lumen within each of housings 12 and 15 (as fully depicted in each of FIGS. 2, 3 and 4 of the following drawings) to combine to make one continuous fluid flow path through the device 10. A first retainer 30 is connected to the distal end of housing 12. In the preferred embodiment of FIG. 1, retainer 30 is shown as a leaf spring having a plurality of leaves, in this embodiment four leaves. The tips of each of the leaves of spring 30 is provided with a generally hemispherical deposit 31 which acts as a safety device to prevent the tips of each leaf or spring 30 from damaging the internal wall of the bladder. A second retainer (not shown in FIG. 1, but present in each of the following figures of the drawings) is adapted to be connected to the proximal end 17 of housing 15 after device 10 has been placed in the urethra of a patient and retainer 30 has opened in the bladder of the patient.

Figure 2:
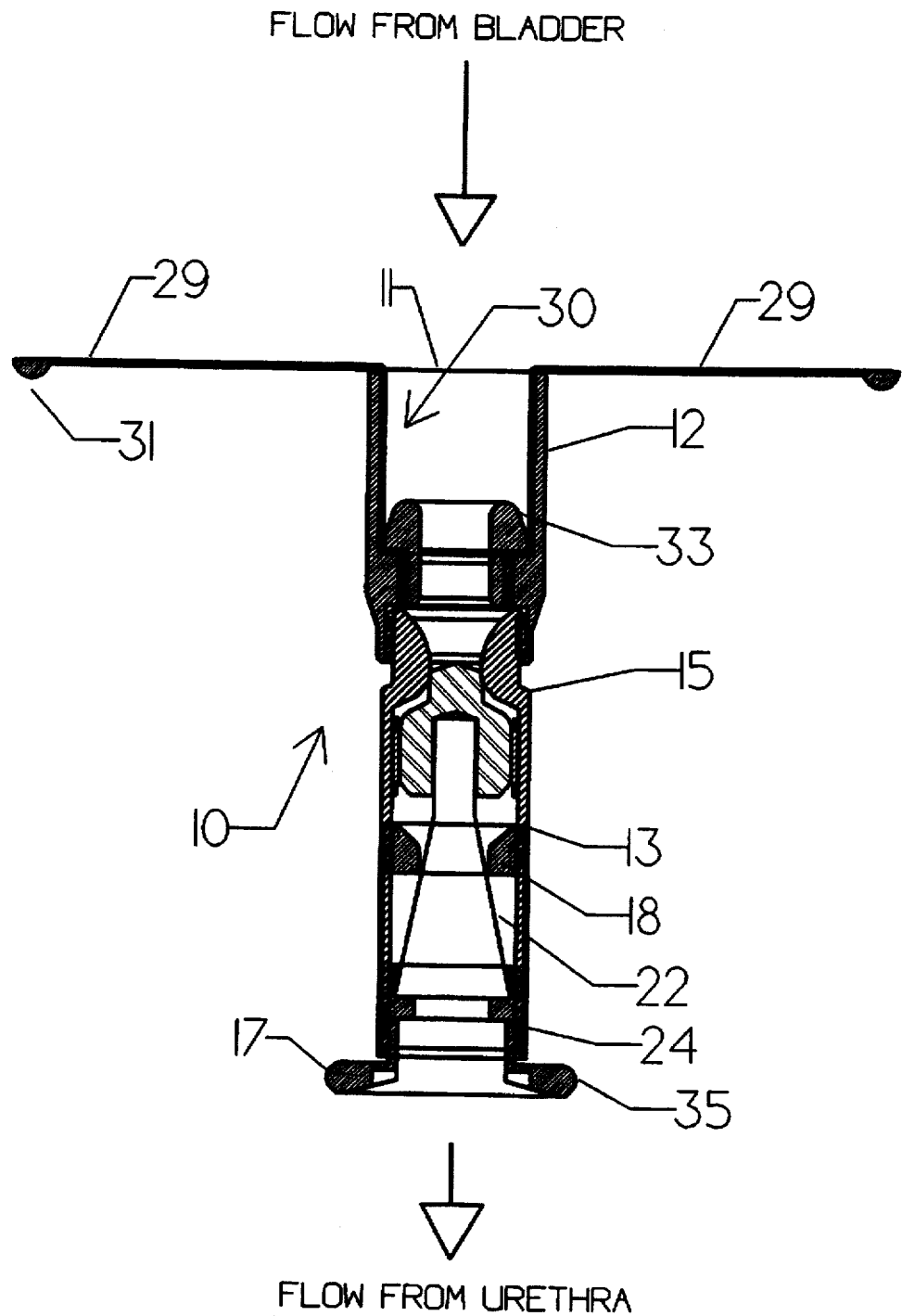
FIG. 2 is a sectioned plan view of the assembled apparatus of this invention.

Referring now to FIG. 2, there is shown a cross-sectional plane view of the assembled apparatus of this invention comprising bladder control device 10. It can be seen that a nut 33, having a central lumen, is used to mount spring 30 within the lumen of housing 12. It can be seen that the leaves of spring or upper retainer 30 are in their uncompressed or extended position, as they would be when inside the bladder of a patient. It can also be clearly seen how safety device 31 takes the form of a hemispherical formation at the tip of each of the leaves of leaf spring or retainer 30.

Also in FIG. 2 it can be seen that within the lumen formed by flow control housing 15 there is mounted a valve assembly for controlling the flow of fluid through the lumen, the assembly comprising a stopper 16, a biasing means or spring 22, a first mounting ring 18 that defines the inner housing chamber within which stopper moves, and a second spring mounting ring 24. The ring 24 is mounted within housing 15 and receives the proximal end of the bias means or spring 22. Ring 18 is mounted for rotational movement within housing 15, and has its distal movement inhibited by a ridge 13 within housing 15. Spring 22 extends through mounting ring 18 and has its distal end connected to stopper 16, which stopper 16 is slidably mounted for movement within the lumen of housing 15.

Also shown in the FIG. 2 depiction of the assembled bladder control device 10 is a second or lower retainer 35. Retainer 35 has a first portion adapted to be connected to the proximal end of housing 15, preferably by a threaded connection. Retainer 35 also has a second section which is significantly wider than either of housings 12 or 15, and thus it will be wider than the urethra after placement of device 10 within the urethral. The second portion or wider portion of retainer 35 is adapted to contact the labia.

As is apparent from the study of FIG. 2, when fluid from the bladder achieves a predetermined pressure, which can be pressure applied by the muscles of the patient, the normal bias of spring 22 will be overcome and stopper 16 will slide proximately to open the valving apparatus to allow the flow of fluid from the bladder through device 10 and from the urethra as indicated by the arrow. It should be noted that nut 33, ring 18, spring 22, ring 24, and retainer 35 all have internal fluid flow paths which align with the axis of the lumens of housings 12 and 15 so that the only major inhibitor of fluid flow from the bladder through the urethra is stopper 16 when it is in place. When stopper 16 is slid proximally by the pressure of the bladder fluid, the stopper 16 is sized such that fluid will flow around it within the lumen of housing 15.

Figure 3:
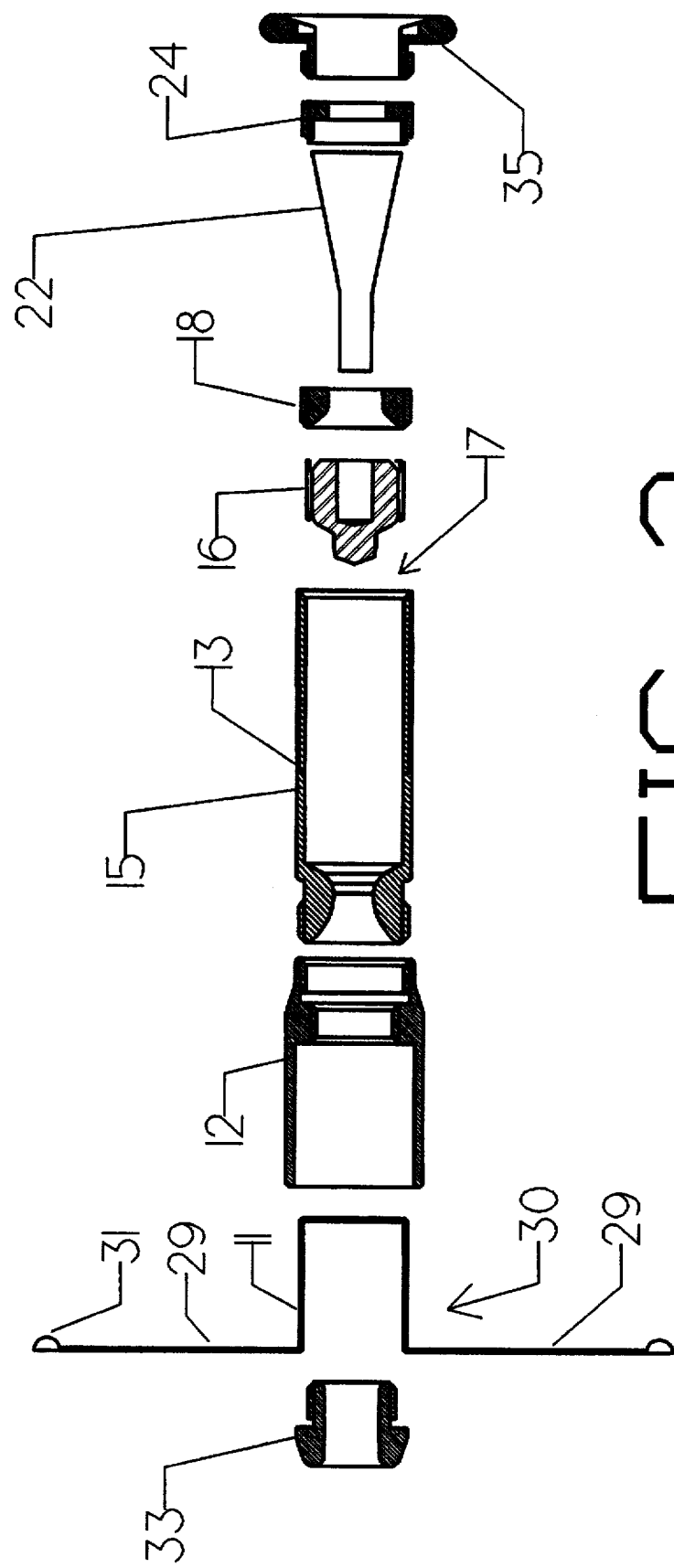
FIG. 3 is an exploded view of the apparatus of FIG. 2.

Referring now to FIG. 3, the apparatus of FIG. 2 is shown in exploded view. Here it can be seen how nut 33 is placed to hold the bladder retaining means or spring 30 within the lumen of housing 12. It can also be seen how housing 15 has its distal end connected to the proximal end of housing 12. It can also be seen how stopper 16 is positioned through the lumen of housing 15 to abut a narrowed inner portion of the lumen of housing 15 and how ring 18 is then slid through the proximal end 17 of the lumen of housing 15 to abut the ridge 13 in the wall of the lumen of housing 15. Spring 22 then has its upper or distal portion placed through the lumen of housing 15, through ring 18 and into connection with stopper 16. Ring 24 is then placed to receive the proximal end of bias means or spring 22 and is pushed through the proximal end 17 of housing 15 and connected within the lumen of housing 15. Finally, after placement of the apparatus of FIG. 3 within the urethra of the patient, the second retainer or lower retainer 35 is threaded into position at the proximal end 17 of housing 15.

As is apparent, when the exploded parts of FIG. 3 are assembled, they will form the assembled device 10 as shown in FIG. 2.

Figure 4:
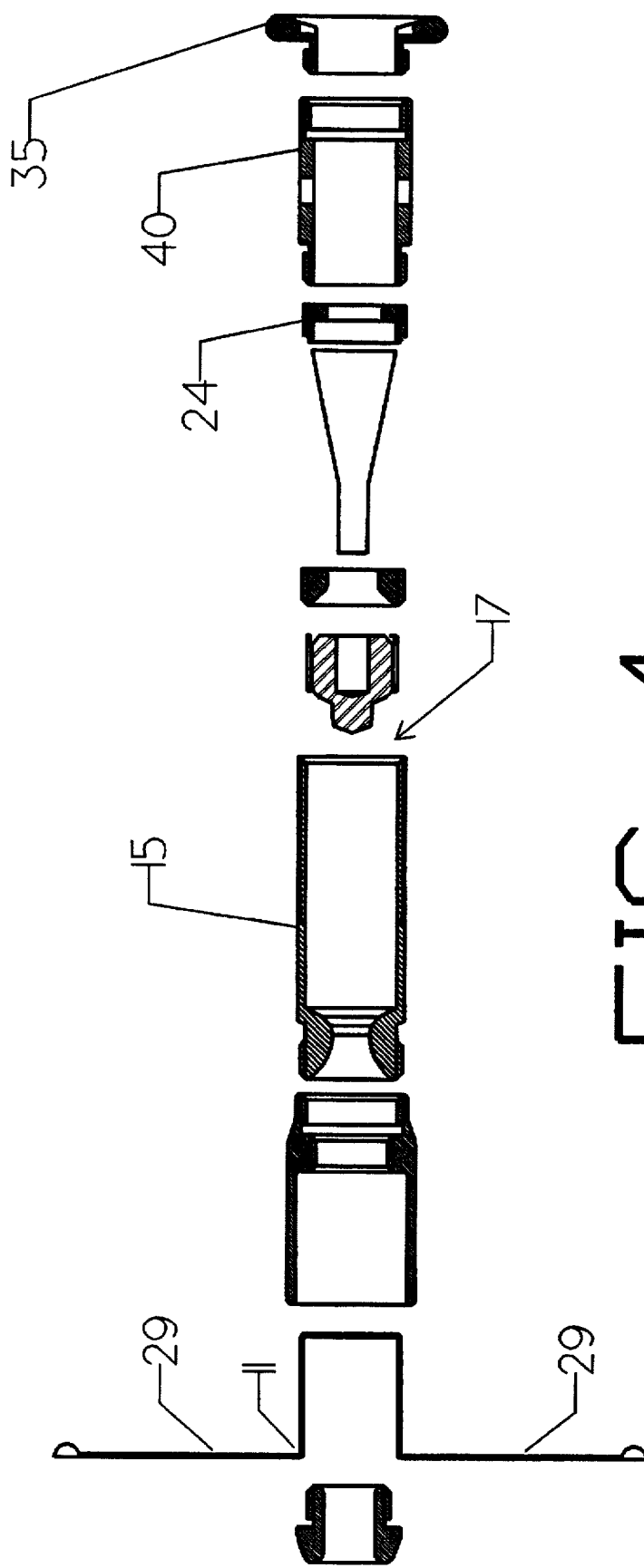
FIG. 4 is an exploded view similar to that of FIG. 3 with an additional extender part added to the apparatus of this invention.

Referring now to FIG. 4 there is shown another exploded view forming yet another embodiment of the apparatus of this invention. It will be apparent from FIG. 4 that all the parts of this embodiment are the same as the parts of FIGS. 2 and 3 with the exception of an extender 40 placed between ring 24 and retaining means 35. Thus when the parts of the spring valving of FIGS. 2 and 3 have been properly placed through the proximal end 17 of housing 15 and are held in place by ring 24, housing 15 is adapted to receive the distal end of extender 40, preferably by threading, and retainer 35 is then connected to the proximal end of extender 40 instead of the proximal end of housing 15. Thus the apparatus of FIG. 4 shows an embodiment of the apparatus of this invention whereby the length of device 10 can be selectively changed by utilizing any one of a number of different sizes of extender 40.

Figure 5:
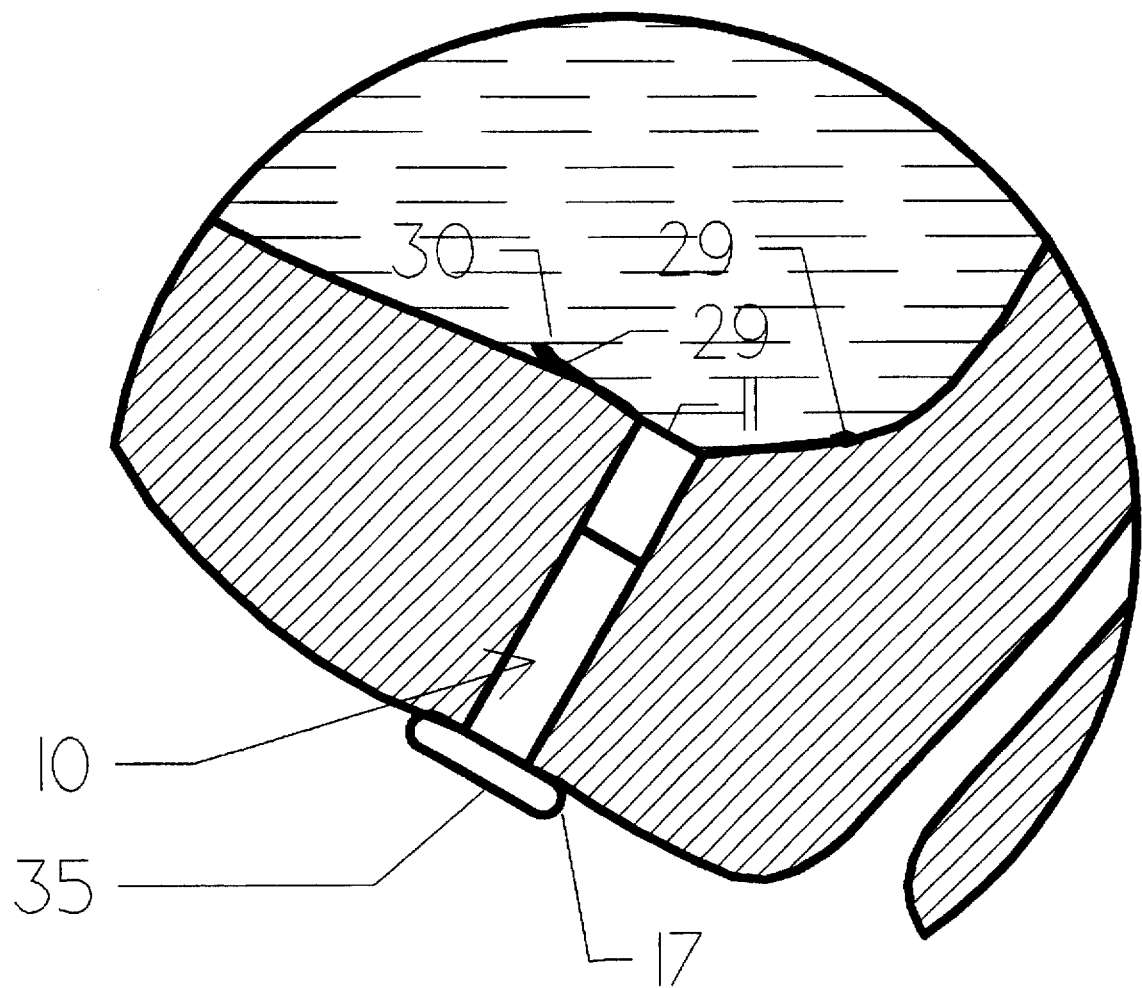
FIG. 5 is a partially sectioned view representative of the urethra and bladder of a patient with the apparatus of this invention shown as retained in the urethra of the patient.

Referring now to FIG. 5 there is shown a partial cross-sectional view representative of the urethra and bladder of a patient. In FIG. 5 the bladder control device 10 is shown after placement in the urethra of the patient and after whatever placement devices which were used have been removed and the urethra has undilated to closely hold and form to the outer surface of device 10. It can be seen how retainer 30 in the form of a leaf spring has opened within the bladder and how the safety devices on the tips of the leaves of spring 30 provide a safety factor to prevent puncture of the bladder wall by the tips of the leaves. Finally, it can be seen how the second or lower retainer 35 when connected to the proximal end of device 10 contacts the labia of the urethra, and how device 10 is thus held within the urethra by retainer 30 and 35 acting at opposite ends of the urethra. It should be recognized that the above-described invention derives its ultimate utility when properly placed within the urethra of the patient. Various prior art methods of dilation of the urethra for placement of a device such as device 10 may be known in the prior art. However, it is believed that the most advantageous apparatus for such placement is fully described in co-pending U.S. application Ser. No., filed, entitled BLADDER CONTROL INSERTION APPARATUS, owned and assigned to the assignee of this invention, and hereby incorporated by reference in this disclosure.

Having thus described the preferred embodiments of the present invention, those of skill in the art will readily appreciate other useful embodiments within the scope of the claims hereto attached.

I claim:

1. Bladder control apparatus for placement in the urethra of a patient comprising:
   a. a retainer housing including a first lumen, and said retainer housing including distal and proximal ends;
   b. a first retainer connected adjacent said distal end of said retainer housing, the first retainer including a leaf spring mounted in said first lumen and including a plurality of leaf springs extending out of said distal end of said retainer housing;
   c. a flow control housing including a second lumen, and said control housing including distal and proximal ends;
   d. a flow control valve mounted in said second lumen;
   e. a second retainer connected adjacent said proximal end of said control housing; and
   f. said distal end of said control housing connected to said proximal end of said retainer housing for aligning said first and second lumens for providing a continuous fluid flow path.

2. The apparatus of claim 1 in which: said plurality of leaves comprises four leaves.

3. The apparatus of claims 1 or 2 including: safety means mounted on each of said plurality of leaves to inhibit damage to the bladder walls.

4. The apparatus of claims 1 or 2 in which said second retainer includes: a first section for selective connection to said control housing proximal end when said control housing is placed within a urethra; and a second section for extending out of and being wider than the urethra, for contact with the urethral labia.

5. The apparatus of claim 4 including: an extender housing including a third lumen, and said extender housing including distal and proximal ends; means for connecting said extender housing distal end to said control housing proximal end; and, means for connecting said second retainer first section to said extender housing proximal end.

* * * * *